US008586350B2

(12) United States Patent
Toujou et al.

(10) Patent No.: US 8,586,350 B2
(45) Date of Patent: Nov. 19, 2013

(54) MECHANISM OF SEPARATING AND PURIFYING DNA AND THE LIKE

(75) Inventors: Osuman Toujou, Takasaki (JP); Masayoshi Ohira, Sayama (JP); Kensuke Okusa, Hanno (JP); Nobuo Seto, Tokorozawa (JP); Masahiro Furuno, Iruma (JP)

(73) Assignee: GL Sciences Incorporated (JP)

( * ) Notice: Subject to any disclaimer, the term of this patent is extended or adjusted under 35 U.S.C. 154(b) by 637 days.

(21) Appl. No.: 10/597,954

(22) PCT Filed: Feb. 12, 2004

(86) PCT No.: PCT/JP2004/001465
§ 371 (c)(1),
(2), (4) Date: Aug. 14, 2006

(87) PCT Pub. No.: WO2005/078088
PCT Pub. Date: Aug. 25, 2005

(65) Prior Publication Data
US 2007/0181482 A1    Aug. 9, 2007

(51) Int. Cl.
| C12M 1/34 | (2006.01) |
| C12M 1/00 | (2006.01) |
| C12Q 1/68 | (2006.01) |
| C07H 21/02 | (2006.01) |
| B01D 15/08 | (2006.01) |
| A23J 1/00 | (2006.01) |
| C03B 23/20 | (2006.01) |

(52) U.S. Cl.
USPC ..... 435/287.2; 435/6.1; 435/283.1; 536/23.1; 210/198.2; 210/656; 210/659; 530/412; 65/36

(58) Field of Classification Search
USPC .............. 435/6.1, 283.1, 287.2; 65/36; 210/198.2, 656, 659; 530/412; 536/23.1
See application file for complete search history.

(56) References Cited

U.S. PATENT DOCUMENTS

| 6,238,565 | B1 * | 5/2001 | Hatch ............................. 435/6 |
| 6,383,393 | B1 | 5/2002 | Colpan et al. |
| 6,855,816 | B1 | 2/2005 | Grimm et al. |
| 2001/0007026 | A1 * | 7/2001 | Kitamura et al. ............ 536/25.4 |
| 2003/0032147 | A1 * | 2/2003 | Sauer et al. .................. 435/91.1 |
| 2003/0148291 | A1 * | 8/2003 | Robotti .......................... 435/6 |
| 2004/0002081 | A1 * | 1/2004 | Urthaler et al. .................. 435/6 |

FOREIGN PATENT DOCUMENTS

| EP | 0 389 063 A2 | 9/1990 |
| JP | 59 227744 | 12/1984 |
| JP | 2-289596 | 11/1990 |
| JP | 2002525558 A | 8/2002 |
| JP | 2002535412 A | 10/2002 |
| JP | 2003144150 A | 5/2003 |
| JP | 2003230380 A | 8/2003 |
| WO | 00/15778 A | 3/2000 |
| WO | 01/83072 A | 11/2001 |
| WO | 02/066135 A1 | 8/2002 |

OTHER PUBLICATIONS

Tennikova et al, An introduction to monolithicdisks as stationary phases for high performance biochromatography, 2000, J. High Resol. Chromatogr., 23, 27-38.*
New England Biolabs pUC18 MSP I digest brochure (down loadded from the internet http://tools.neb.com/NEBcutter2), printed on Jun. 15, 2011, p. 1.*
Podgornik et al., Application of Very Short Monolithic Columns for Separation of Low and High Molecular Mass Substances, Journal of Liquid Chromatography & Related Technologies, 2002, pp. 3099-3116, vol. 25, No. 20.
Lubbad et al., Micropreparative fractionation of DNA Fragments on Metathesis-based Monoliths: Influence of Stoichiometry on Separation, Journal of Liquid Chromatography A, 2002, pp. 121-129, 959.
Walcher et al., Monolithic Capillary Columns for Liquid Chromatography-Electrospray Ionization Mass Spectrometry in Proteomic and Genomic Research, Journal of Chromatography B, 2002, pp. 111-125, vol. 782.
Kristensen, et al.; Nucleic Acids Research; 1987; 5507-5516; vol. 15, No. 14; Oxford, England.
Vogelstein et al.; Preparative and analytical purification of DNA from agarose; Feb. 1979; Proc. Natl. Acad. Sci. USA; vol. 76, No. 2; 615-619.
Marko et al.; A Procedure for the Large-Scale Isolation of Highly Purified Plasmid DNA Using Alkaline Extraction and Binding to Glass Powder; 1982; Analytical Biochemistry, 121; 382-387.
Maniatis et al.; Molecular Cloning, A Laboratory Manual; 1982; 188-190; USA.

(Continued)

*Primary Examiner* — Narayan Bhat
(74) *Attorney, Agent, or Firm* — Hahn Loeser & Parks LLP; John J. Cunniff (57) ABSTRACT

A high-purity fragment is obtained by a simple mechanism and method for separating and purifying a nucleic acid, particularly fragment DNA, extremely efficiently and with a high reproducibility, wherein elution with a high-concentration salt is not performed and necessity of elution and purification is eliminated.
This mechanism is a mechanism for purifying a nucleic acid, particularly fragment DNA using a monolith structure formed with glass or silica, specifically, an integral porous body having an open structure with pores that communicate the upper end with the lower end, wherein through-pores corresponding to nucleic acid sizes of 35 bp (mer) to 100 Kbp (mer) are provided.

4 Claims, 7 Drawing Sheets

(56) References Cited

OTHER PUBLICATIONS

Branovic K et al, Application of short monolithic columns for fast purification of plasmid DNA, Journal of Chromatography B: Biomedical Sciences & Applications, vol. 801, No. 2, Jan. 13, 2003, pp. 331-337, Elsevier, Amsterdam, NL.

Motokawa M. et al, Monolithic silica columns with various skeleton sizes and through-pore sizes for capillary liquid chromatography, Journal of Chromatography A, Elsevier, vol. 961, No. 1, Jun. 28, 2002, pp. 53-63, Amsterdam, NL.

Tian H et al, Evaluation of silica resins for direct and efficient extraction of DNA from complex biological matrices in a miniaturized format, Analytical Biochemistry, Aug. 1, 2000, vol. 283, No. 2, pp. 175-191.

EP 04 71 0506 Supplementary European Search Report dated Apr. 2, 2007.

\* cited by examiner

MECHANISM OF SEPARATING AND PURIFYING DNA AND THE LIKE

TECHNICAL FIELD

The present invention relates to a mechanism of separating and purifying DNA and the like.

BACKGROUND ART

Hitherto, it has been well known that in a method for purification and separation of a nucleic acid from a nucleic acid-containing material, a nucleic acid mixture is adsorbed on particles of glass and silica gel, glass, silica wool, silica, a glass membrane, a polymer or the like under the presence of chaotropic agents. The nucleic acid-containing material is mainly a biological raw material such as cultured cells and tissues, body fluids including blood, serum, urine and feces, germs including bacteria and human Mycobacterium tuberculosis, or viruses of HIV, hepatitis B and hepatitis C, and plasmid DNA, genomic DNA, chromosomal DNA, RNA, mitochondrial DNA, fragment DNA and the like can be separated and purified.

Purification of fragment DNA is a technique that is very frequently used in molecular biological studies, and conducts prior to PCR, cloning, sequencing, restriction enzyme digestion and applications of other enzymatic actions and the like.

For example, there is a method of isolating DNA from a recombinant M13 phage, and an isolation method in which M13 phage DNA binds on a glass fiber filter by adding chaotropic agents and then eluted via separation, washing and drying is shown in Nucleic Acids Research Vol. 15 5507-5516 (1978).

In a method in which a glass powder is added, DNA binds to the glass powder, centrifugal separation is performed, the glass powder is collected and washed, and DNA is eluted and isolated is shown in Pvoc. Natl. Acad. Sci. USA Vol. 76, 615-619 (1979). A similar method is described in Japanese Patent Laid-Open No. 59-227744, Analytical Biochemistry Vol. 121.382-387 (1982), Molecular cloning: A Laboratory Manual 188-190 (1982) and so on.

A method in which a composite biological starting material, chaotropic agents and a nucleic acid binding solid phase including silica or a derivative thereof are mixed, the solid phase to which a nucleic acid binds is separated from a liquid, and washed to elute the nucleic acid is proposed in Japanese Patent No. 2680462.

The physical mechanism of adsorbing DNA and RNA under the presence of chaotropic agents has not been clarified for its details, but it is believed that a cation exchange reaction occurs between a negatively charged carrier and a nucleic acid. Thus, the efficiency of purification can be considered to be equal to the efficiency of contact between the surface of the carrier and a biological sample.

Irrespective of which of the above described carriers is used, a procedure in which a carrier on which a nucleic acid is to be adsorbed is held in a container (cartridge, chip or the like), and a biological sample is passed through the container, a nucleic acid is adsorbed on the carrier with an adsorption buffer solution, contaminants other than nucleic acid components are then expelled to outside the cartridge with a washing liquid, and an elution liquid is then passed to take out the nucleic acid components with the liquid is general.

In addition, purification of fragment DNA from an agarose gel by electrophoresis and various extractions is often performed, but this method requires much time, and the obtained DNA is extremely thin, contains salts and organic solvents, and is therefore required to be further desalted or concentrated by ethanol precipitation. In a conventional method such as a gel filtration purification technology, it is very difficult to separate molecules having similar molecular weights.

These separation methods using a carrier require use of high-concentration salts, and therefore a phenomenon causing decomposition or degradation of DNA on the surfaces of particles of glass or silica gel has been confirmed. The adsorption occurs substantially quantitatively under the presence of high-concentration chaotropic agents, but elution of adsorbed DNA is carried out under the presence of a buffer solution of the salts. The treatment of fractions of DNA is limited to a range of 100 base pairs (bp) to 10000 base pairs (bp), and it is impossible to quantitatively separate or purify DNA fractions with 100 base pairs (bp) or less or DNA with 10000 to 100000 base pairs (bp).

For a method based on a glass powder (glass beads) as a carrier, it is conceivable that beads are downsized or the amount of beads is increased for improving the efficiency of contact between the surface of the carrier and a nucleic acid. However, a pressure during passage of a liquid increases, the operability is considerably impaired, and air gaps between beads become so small that nucleic acid molecules cannot enter the air gaps because of their large molecular weight, resulting in a problem of reducing the efficiency contrarily. If the length of the container is increased for the purpose of improving the separation, the pressure increases, and in addition, the amount of eluted solvent increases to reduce the efficiency of concentration, leading to a process which is less convenient. Further, if the bead or wool is used, its fragments and particles enter an elution liquid although the amount is very small, thus causing a problem in a subsequent application. If a packing method for packing the carrier in a container is not fixed, separation time and the pattern are changed, and therefore a problem of poor stability of separation arises.

A method using a membrane or a filter as a carrier has an advantage that it can be processed for improved usability, but it is difficult to form pores appropriate to separation with control, and the method is thus poor in practicality.

A method using a polymer resin is not capable of purification with a simple protocol, since a separation system is complicated such that an action of reacting specifically with a nucleic acid depending on the property of the polymer resin or a part having an influence exists in addition to the concerned part.

In any case, high-purity fragment DNA cannot be purified. There are disadvantages of difficulty of handling unique to a powder silica resin and a suspension, hindrance of a subsequent application reaction, and so on.

As in the invention of Japanese Patent No. 2680462, the concept of direct isolation of a nucleic acid from a complicated starting material without a pretreatment refers to "digestion" and "purification" being performed at the same time. As a result, drawbacks of requiring a radical reaction condition and reducing a range of applicable molecular weights of nucleic acids are yielded.

In Japanese Patent laid-open No. Heisei 8-501321, a method is proposed in which a nucleic acid mixture is adsorbed on a porous or nonporous inorganic base such as silica gel or glass from an adsorption aqueous solution containing high-concentration (ionic strength) salts and an organic acid such as an aliphatic alcohol or polyethylene glycol, washed and then eluted with a solution containing lower-concentration (ionic strength) salts to obtain a nucleic acid.

However, in this method, a nucleic acid mixture is adsorbed on an inorganic material from an adsorption aqueous solution containing high-concentration salts and a nucleic acid is eluted with a solution containing salts although its concentration is low, and therefore if, for example, a DNA sample is included in large agarose fractions, it is necessary to treat the sample using a plurality of columns, and eluted fragment DNA is pooled, and further, obtained fragment DNA contains salts and organic solvents, and therefore operation steps of concentration, desalination and the like are required, and moreover, purified DNA may be lost during ethanol precipitation.

DISCLOSURE OF THE INVENTION

Thus, the present invention is to propose a method of high reproducibility in which the aforementioned aspects of prior arts are improved so that adsorption and elution separation can be performed extremely simply and easily, elution with high-concentration salts are not carried out, purification after elution is not required, and the efficiency of separation and purification of nucleic acids, especially fragment DNA or the like is extremely enhanced. Such a method involves an integral monolith structure, characterized in that through-pores continuously extending from one end to the other end and corresponding to nucleic acids of sizes of 35 bp (mer) to 100 Kbp (mer) are provided and configured so that nucleic acids corresponding the through-pores can be retained, respectively, by allowing a solution containing nucleic acids to be separated to pass therethrough, characterized in that the monolith structure employs an inorganic material such as glass or silica or a hybrid material containing an organic material and an inorganic material, which is a porous body having macro-pores (through-pores) penetrating from the upper surface to the lower surface, characterized in that the porous body of the monolith structure has micro-pores (meso-pore) in the macro-pores (through-pores), characterized in that the porous body of the monolith structure has a macro-pore (through-pore) size of 1 to 100 μm and a micro-pore (meso-pore) size of 0 to 100 nm, characterized in that a disc formed with the monolith structure is placed in a column tube to form a monolith solid phase column, and characterized in that the structure employs a monolith solid phase column formed by detachably attaching a base formed with the monolith structure to a cylindrical body having the top and the bottom opened.

According to the present invention, a wide range of DNA fractions of 100 bp (mer) or less and DNA fractions of 10000 bp (mer) to 100 Kbp (mer) can be separated quantitatively and purified efficiently. Nucleic acids can be adsorbed and separated without using a radical react ion condition dissolution and adsorption with high-concentration salts are not required, operations of concentration and desalination are not required, and purification of nucleic acids, especially purification of fragment DNA is easy. The nucleic acid can be eluted with a solution having no salts or a sterile water, and high-purity fragment DNA is easily obtained.

BEST MODE FOR CARRYING OUT THE INVENTION

The present inventors have found that if an efficient monolith structure is used and a buffer condition is adjusted, use of a buffer having high salts concentration, which has been considered as a normal practice, becomes unnecessary. There is only water besides tris hydrochloric acid EDTA added for preservation of a nucleic acid, and the nucleic acid is decoupled from a carrier on which it has been adsorbed, and is eluted. When adsorbing a nucleic acid, salts compound providing ions considered reacting with isopropanol and silanol groups acting as a separation solvent, a guanidine hydrochloride as a chaotropic salt for dissolving an agarose gel, and the like are used as an adsorption solvent. At this time, it is conceivable that if an alkali metal salt which is easily changed into a positive ion exists, a dehydrogenation reaction easily occurs, whereby the positive ion causes a cation crosslinking reaction with a phosphoric acid part of a nucleic acid to adsorb the nucleic acid. The alkali metal is, for example, lithium, sodium, potassium, rubidium, cesium, francium or the like. Among them, a potassium salt, which has a low electronegativity and is easily changed into a positive ion to undergo a cation crosslinking reaction, is useful, since it easily undergoes a reaction, and does not hinder a subsequent application although it is ultimately eluted in an ionic state along with nucleic acid components. A sodium salt is not very useful, since it hinders a subsequent application, and therefore cannot be used unless a desalination operation is carried out. In other words, the apparatus and method allow the obtained purified liquid to be brought directly to subsequent operations (PCR, cloning, sequencing and enzymic operations) without requiring the desalination, alcohol precipitation and the like. It is very important to simplify the operation procedure for preventing damages in nucleic acids.

It is an aspect of the present invention to provide a method allowing nucleic acids to be purified without affecting various kinds of subsequent application operations such as cloning by using silica or glass having a monolith structure having high purification efficiency and using a more simple buffer solution.

The monolith structure refers to an integral porous body having macro-pores (through-pores) with an open structure that communicate the upper end with the lower end. The monolith structure have macro-pores (through-pores) and/or meso-pores (micro-pores) in the skeletal structure forming the macro-pores.

The monolith structure can be prepared mainly by a sol-gel method. Specifically, a metal alkoxide is partially hydrolyzed to prepare a reactive monomer, this monomer is subjected to polycondensation to prepare a colloidal oligomer (production of sol), the oligomer is further hydrolyzed to promote polymerization and crosslinking, and a three-dimensional structure is thereby prepared (production of gel) to synthesize the monolith structure.

An organic and inorganic hybrid monolith can easily be prepared if various kinds of organic monomers are added at the time of the reaction. Thus, a chemical property can also be added depending on the type of organic monomer added. For example, by adding an organic monomer having a hydrophilic group, the water absorption property of an aqueous sample component can be improved. By adding an organic monomer having a functional group showing a selective chemical action is added, the organic monomer is used for adsorption of characteristic components as impurities in purification, and the impurities are left on a solid phase, whereby the efficiency of purification of a nucleic acid can be improved. By putting a polymer having a high elastic modulus in a sol-gel step, the monolith structure can be made to have elasticity. Further fundamentally, organic and inorganic materials can be made to coexist to improve the chemical stability of the monolith structure.

These respects mean that for an organic and inorganic hybrid monolith structure prepared by the sol-gel method, properties of forming a chemical surface appropriate to a purpose based on the type of organic monomer added and improving the chemical stability can be added, and indicates that monolith properties effective in pretreatment of DNA can be improved freely in accordance with a purpose. Further, a monolith prepared by the sol-gel method is suitable in that it contains only a small amount of metal as a solid phase for DNA of the present invention. General silica gel or the like is prepared from sodium silicate or the like, and a large amount of metal remains. Certainly, there are some cases where silica gel is prepared from purified sodium silicate and high-purity silica gel is prepared by the sol-gel method, but those silica gels are so expensive that they are not suitable for single use as a normal usage form. Even if they can be produced inexpensively, batch type synthesis is performed at the time of preparation of particles, and there is a high possibility that metal concentration occurs from a synthesis atmosphere.

In synthesis of the monolith structure in the sol-gel method, silica gel is prepared by continuous steps, and there is no contamination of a metal. In silica gel, measures of washing with hydrochloric acid, nitric acid or the like, and so on have been taken, or EDTA for reducing influences of a metal has been added, but these measures are not required at all in the solid phase of the present invention.

As another method, a monolith structure solid phase can also be prepared by a glass part phase. Fundamentally, this method is comparable in effectiveness to synthesis of the monolith structure by the sol-gel method, but is effective when forming secondary micropores on the inner surface, since a macropore can be formed in a large size as compared to the sol-gel monolith. Further, there is an advantage that the glass part phase has a high alkali resistance owing to its composition and thus can be regenerated by alkali washing.

The present invention will be described in detail below with examples shown in the figures.

The most basic configuration in the present invention consists in adsorbing fragment DNA on glass or silica under the presence of chaotropic agents for purifying fragment DNA from agarose gel, a PCR reactant, restriction enzyme treated DNA, single-strand DNA, RNA or the like, and particularly, using a monolith structure formed by glass or silica having an excellent separation capability, specifically an integral porous material having an open structure with pores that communicate the upper end with the lower end, and adsorbing the DNA on the porous material.

Adsorption of fragment DNA on glass or silica under the presence of chaotropic agents has already been proposed and practiced.

However, in the conventional method, packing material (particles) is always used. Thus, there are disadvantages that the packing material is not evenly packed, particles remains in a DNA solution after passage of packing material, the area of contact with the liquid is so small that the reaction efficiency is poor, and the liquid passage pressure is so high that handling is difficult.

The present invention is in part in common with the conventional technique in that components adsorbed on glass or silica gel particles from agarose gel and a PCR reactant under the presence of chaotropic agents are extracted.

In this conventional technique, adsorption is made to occur quantitatively under the presence of high-concentration chaotropic agents, and elution of an adsorbed nucleic acid is carried out at lower salts concentration.

Moreover, in the method of National Publication of International Patent Application No. 8-5011321 separation of a nucleic acid is carried out in one operation step without a step of preliminarily purifying a nucleic acid to be separated. Thus, a radical reaction condition by a buffer of a high-concentration salt is required, and a range of applicable molecular weights of nucleic acids is reduced. Further, purified DNA is extremely thin, contains salts and organic solvents, and is therefore required to be further subjected to ethanol precipitation and concentration.

In the present invention, which makes improvements for these disadvantages, adsorption or elution is not performed with high-concentration salts, but elution is performed with water. As a result, a sample having a very high concentration and requiring no additional purification is obtained.

The present invention has as one aspect, purification of DNA fragments from agarose gel and fragment DNA and the like from a PCR amplification reaction DNA solution and an enzyme reaction solution.

In the present invention, DNA fragments with 35 bp to 100 Kbp can be extracted and purified from standard agarose gel or low-melt agarose gel prepared with a Tris acetic acid (TAE) buffer or a Tris boric acid (TBE) buffer, and a recovery rate of 60 to 80% can be obtained. In addition to extraction from gel, a PCR product with 35 bp to 100 Kbp can be purified directly from a PCR reactant, and a recovery rate of 80 to 95% can be obtained. The obtained fragment DNA contains neither salts nor organic solvents, and therefore it is not necessary to carry out ethanol precipitation, desalination and concentration. This product is a monolith based system, the DNA binding capability is 5 to 8 µg at the maximum, and isolated fragment DNA can be collected in only five minutes.

In the case of purification from gel, a desired DNA band is cut out from gel after electrophoresis, and dissolved under the presence of guanidine thiocyanic acid (dissolution and adsorption buffer). In the case of purification after PCR amplification, an adsorption buffer is added directly to PCR reactant. Dissolved gel fractions are passed through a monolith solid phase column using a micro centrifugal machine or a vacuum apparatus. At this time, desired DNA binds to the surface of a silica monolith or a glass monolith, the coupled fragment DNA fractions are washed with a washing buffer, and DNA is eluted with water (elution buffer).

As these buffers, the following buffers are used.
Buffer A (dissolution and adsorption buffer)
Buffer B (washing buffer)
Buffer C (elution buffer or sterile water)
These buffers will be described further in detail below.
Buffer A1 for PCR reactant (guanidine hydrochloride: 1 to 8 M; potassium acetate: 0.1 to 1 M; 2-propanal: 1 to 70%)
Buffer A2 for agarose gel (guanidine thiocyanic acid: 1 to 8 M; potassium acetate: 0.1 to 1 M; 2-propanal: 1 to 70%)
Buffer B (potassium acetate: 0.1 to 1 M; ethanol: 1 to 80%)
Buffer C (pH=8 to 8.5; Tris-HCl 10 mM; EDTA 1 mM; or sterile DNA/RNA free water)

In the buffer A1, guanidine thiocyanic acid is suitable as a guanidine hydrochloride, and the amount thereof is more preferably 1 to 8 M. The efficient amount of 2-propanol is 40% or more.

In the buffer A2, the above conditions apply.

In the elution buffer C, elution with water is possible, but for preventing entrance of bacteria, use of RNase free treated with an ultrafiltration membrane or diethyl pyrocarnate is recommended. If purified DNA is stored, water to which an EDTA buffer has been added may be used as the elution buffer C for preventing increase of bacteria. The efficiency of purification does not vary depending on presence/absence of the EDTA buffer from a viewpoint of a separation mechanism.

In the invention of this application, use of a monolith structure for a base allows a reaction between a phosphoric acid group of a nucleic acid and a silanol group to proceed efficiently. The problem of carryover of silica particles which is unavoidable when using particulate packing material and which may hinder so called an application reaction as a result of purification with silica particles deposited on a sample can be prevented. Further, there are advantages that the pressure during separation is kept low, and unlike a case where packing material is used, no sealing parts are required, and so on.

This monolith structure can be prepared by, for example, so called a sol-gel method in which low-molecular compound sol capable of polymerizing an inorganic porous material such as silica gel is purified, and finally, gel of an aggregate or polymer is obtained. In this method, the central macro-pore (through-pore) diameter is generally 1 to 100 µm, but can be several nm owing to subsequent technological advancement.

A monolith structure having pores in a silica body having two kinds of pores can be prepared using spinodal decomposition in a sol-gel process.

A porous body having a structure in which porous materials having micro-pores having an open structure are filled in a macropore extending from the upper surface to the lower surface can be prepared. In this connection, in this porous body, the diameter of the macro-pore is 1 to 100 µm and the diameter of the micro-pore is 0 to 100 nm.

In addition, an appropriate monolith structure can be used as a matter of course as long as it is formed by including glass or silica.

In this monolith structure, the through-pore (macro-pore) of the porous body can be formed as desired according to the method of production of the structure, and is therefore appropriately selected and formed, but the diameter of about 1 to 100 µm leads easy use. However, this selection depends on raw materials to be used, for example agarose gel, a PCR reaction solution and a buffer, and the purpose thereof.

For description of one form of use of a base constituted by this monolith structure, a cylindrical column tube 1 is formed, and a closable cap 3 is detachably provided in an upper end opening portion 2. A small-diameter outlet 4 is formed at the lower end, and in the upper part of the outlet 4, a step 5 is provided to form a medium aperture portion 6. A disc 7 as the base formed of the monolith structure can be placed on or fitted to the step 5. The disc 7 may be formed in a discal form having a shape substantially same as that of the medium aperture portion 6 and having a desired thickness of, for example, about 0.1 to 10 mm, or in a conical form as desired. A monolith solid phase column 9 is formed by the column tube 1 and the disc 7. Reference numeral 8 denotes a collection tube, which is configured to have a diameter allowing the column tube 1 to pass therethrough and configured such that the upper end edge of the column tube 1 can be fixed in the upper part.

Figure 9:
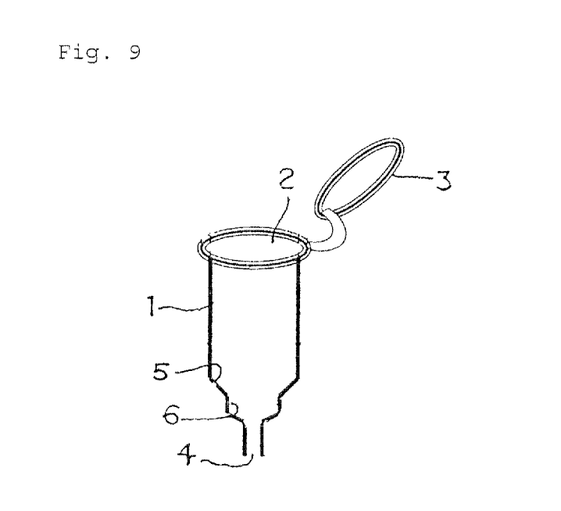
FIG. 9 is a perspective view for explaining a column tube in one example of the present invention.
Figure 11:
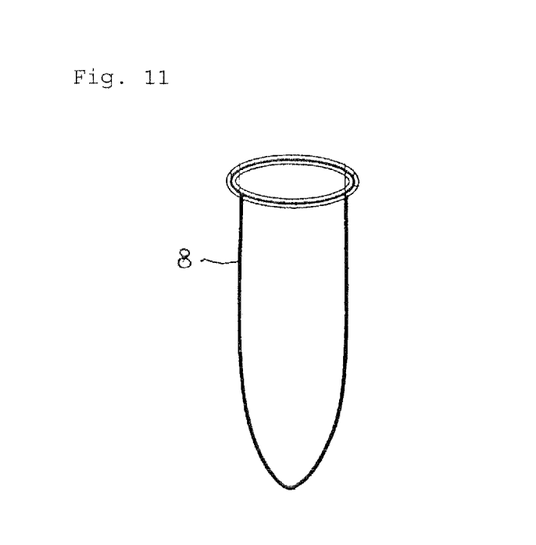
FIG. 11 is a perspective view for explaining a collection tube in one example of the present invention.

For the above described column tube 1 and collection tube 8, tubes made of polypropylene are used, but any other material having good visibility and a certain degree of strength, such as an organic polymer having no influence on a nucleic acid, for example polyethylene, polyethylene terephthalate or polystyrene, or an inorganic polymer, for example glass or silica may be used.

Figure 10:
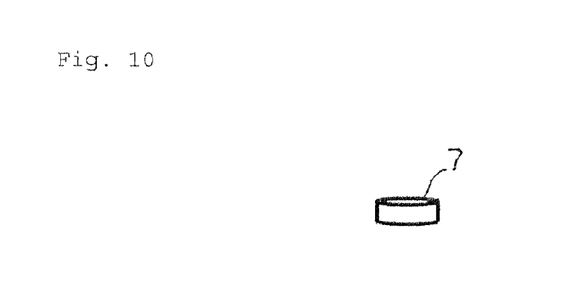
FIG. 10 is a perspective view for explaining a disc in one example of the present invention.

The disc 7 is specified as the base of the monolith structure, but the base is not limited thereto, and can be used in a shape of for example, a dish or a cylinder, which allows a solution to freely pass.

The molecular size of DNA is said to be about 3.4 nm per 10 base pairs. It is conceivable that for example, if the macro-pores have a diameter of about 10 nm to 100 nm in DNA with 35 bp to 300 bp, the macro-pores have a diameter of about 100 nm to 1 µm in DNA with 300 bp to 3 Kbp, the macro-pores have a diameter of about 1 µm to 10 µm in DNA with 30 Kbp to 300 Kbp, and the macro-pores have a diameter of about 10 µm to 100 µm in DNA with 30 Kbp to 300 Kbp, DNA molecules can be allowed to pass without damaging or collapsing DNA molecules.

For improving the interaction with impurities and the like and performing purification more efficiently, micro-pores are added. From experiences of various kinds of tests and experiments, it has been confirmed that an interaction with a compound having a molecular weight of several hundreds of thousands occurs if the micro-pore has a diameter of around several tens of nm and an interaction with a compound having a molecular weight of several hundreds to several tens of thousands if the micropore has a diameter of around 10 nm, and it has been known that for a compound having a larger molecular weight, it is preferable that the micropore which is said to contribute to collapse of the molecules is almost absence, specifically the micropore has a diameter of 0 nm.

Several kinds of integral monolith structures having micropores added to a macro-pore can also be prepared and used properly according to the type of DNA and the purpose of removal of impurities, and the like. In this connection, for preparing several kinds of integral monolith structures, a method in which a macropore is prepared beforehand, and micropores are then formed is more convenient in terms of synthesis.

In purification that is currently required, separation and purification from low molecule compounds such as primers and agarose gel decomposition products is dominant, and separation can sufficiently be performed with one kind of monolith structure.

If a monolith structure in which a macro-pore having a diameter of 1 to 100 µm, preferably about 20 µm and micropores having a diameter of 0 to 100 nm, preferably about 10 nm are formed is used, a wide range of DNAs with 35 bp (mer) to 100 Kbp (mer) shown in examples can sufficiently be purified.

A. The Following Method is Used for Producing a PCR Product using a Monolith Solid Phase Column.

1. Micro-Centrifugation Method

This protocol is designed for the purpose of purifying a double-strand DNA fragment from a PCR reaction solution, and use of a monolith solid phase column and buffers for purification allows a fragment (PCR products) with 35 bp to 100 Kbp to be separated from a primer, a nucleotide, a polymerase, salts or the like by a centrifugal operation.

100 µl of buffer A1 (adsorption buffer) is added to 10 µl of PCR reaction solution. About 300 µl of buffer B (washing buffer) is used for washing.

All centrifugal operations are carried out by a general desktop micro centrifugal machine at 10000 rpm or less.

1. 10 parts by volume of buffer A1 are added to 1 part by volume of PCR reaction solution and mixed. It is not necessary to remove mineral oil. For example, 500 µl of buffer A1 is added to 50 µl of PCR reaction solution (amount not including the amount of oil).

Figure 12:
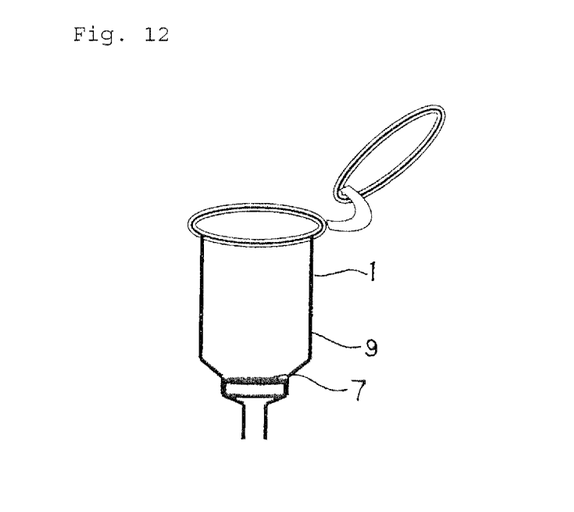
FIG. 12 is a perspective view for explaining a monolith solid phase column in one example of the present invention.

2. The monolith solid phase column 9 is inserted into the collection tube 8, and a prepared sample is applied to the monolith solid phase column. For obtaining a high recovery rate, the sample solution is added to the monolith solid phase column 9 in its entirety.

3. The monolith solid phase column 9 attached to the collection tube 8 is centrifuged at 10000 rpm for 30 seconds, the monolith solid phase column 9 is then detached, and a liquid in the collection tube 8 is removed. The monolith solid phase column 9 is inserted into the collection tube again.

4. 500 µl of buffer B (washing buffer) is added, and the monolith solid phase column 9 is centrifuged at 10000 rpm for 30 seconds. The monolith solid phase column 9 is further centrifuged at 10000 rpm for 1 minute.

For fully removing remaining ethanol originating in the buffer after discarding the liquid in the collection tube 8, it is necessary to carry out a centrifugal operation again.

5. The monolith solid phase column 9 is taken into a new 1.5 ml centrifugal sampling tube, 10 to 50 µl of buffer C (elution buffer) is added to the center of the monolith surface, and the monolith solid phase column 9 is incubated at room temperature for 1 minute, and then centrifuged at 10000 rpm for 1 minute. The DNA eluted into the centrifugal tube is purified DNA, which is stored at −20° C. Alternatively, the DNA is used directly for a subsequent operation.

The elution buffer C is added to the central portion of the monolith surface so that DNA bound to the monolith is fully eluted. If 10 µl of elution buffer C is used, the amount of eluent is 9 µl.

The elution efficiency becomes a maximum when pH is in a range of 8 to 8.5. If sterile water is used for elution, it should be ensured that pH is in this range.

2. Vacuum Manifold Method

The monolith solid phase column can be operated by a vacuum manifold including a general lure adaptor. This protocol is designed for the purpose of purifying a double-strand DNA fragment from a PCR reaction solution. Use of a monolith solid phase column and buffers for purification allows a fragment (PCR products) with 35 bp to 100 Kbp to be separated from a primer, a nucleotide, a polymerase, salts or the like by a sample treatment operation by the suction apparatus.

100 µl of buffer A1 (adsorption buffer) is added to 10 µl of PCR reaction solution. About 300 µl of buffer B (washing buffer) is used for washing.

A vacuum switch is temporarily turned off for each operation step so that uniform and stable vacuum is accomplished.

10 parts by volume of buffer A1 are added to 1 part by volume of PCR reaction solution and mixed. It is not necessary to remove mineral oil. For example, 500 µl of buffer A1 is added to 50 µl of PCR reaction solution (amount not including the amount of oil).

2. A vacuum manifold and a monolith solid phase column are prepared. A lure adaptor vacuum manifold is connected to a vacuum apparatus.

3. A vacuum adaptor attached to a port on the vacuum manifold is mounted. The monolith solid phase column 9 is inserted into the vacuum adaptor.

4. An prepared PCR sample is applied to the monolith solid phase column 9 by a pipette, and vacuumed for binding DNA. The solution is vacuumed until it completely passes through the monolith solid phase column 9. After the sample passes through the column, the vacuum is stopped.

For obtaining a high recovery rate, the sample solution is added to the monolith solid phase column 9 in its entirety. The maximum added amount is 800 µl, and if the amount of sample is greater than 800 µl, the sample is added in several portions.

5. 500 µl of buffer B (washing buffer) is added to the monolith solid phase column 9, and vacuumed until the liquid passes through the monolith solid phase column.

6. The monolith solid phase column 9 is detached from the manifold, and taken into the collection tube 8. The monolith solid phase column 9 is centrifuged at 10000 rpm for 1 minute.

The centrifugal operation is necessary for completely removing remaining ethanol originating in the buffer. (The liquid is suctioned until it passes through the monolith solid phase column, and the monolith solid phase column is dried. This is necessary means for completely removing the washing buffer remaining in the monolith solid phase column 9.)

7. The monolith solid phase column 9 is taken into a new 1.5 ml centrifugal sampling tube, 10 to 50 µl of buffer C (elution buffer) is added to the center of the monolith surface, and the column is incubated at room temperature for 1 minute, and then centrifuged at 10000 rpm for 1 minute. The eluted DNA in the centrifugal tube is purified DNA, which is stored at −20° C. Alternatively, the DNA is used directly for a subsequent operation.

The elution buffer C is added to the central portion of the monolith surface so that DNA bound to the monolith is fully eluted.

If 10 µl of elution buffer C is used, the amount of eluent is 9 µl.

The elution efficiency becomes a maximum when pH is in a range of 8 to 8.5. If a sterile water system is used for elution, it should be ensured that pH is in this range.

B. The Following Method is Used for Purifying Agarose Gel using the Monolith Solid Phase Column 9.

1. Micro-Centrifugation Method

This protocol is designed for the purpose of purifying a DNA fragment from standard or low-melt agarose gel (using TE or TEE buffer), and use of a monolith column and buffers for purification allows a fragment with 35 bp to 100 Kbp to be separated from a primer, a nucleotide, a polymerase, salts or the like by a centrifugal operation. A maximum of 1000 mg of agarose can be treated for one monolith column.

10 µl of buffer A (dissolution and adsorption buffer) is added to 10 mg of agarose gel. About 500 µl of buffer B (washing buffer) is used for washing.

All centrifugal operations are carried out by a general desktop micro centrifugal machine at 10000 rpm or less.

1. A target band is cut out by a clean razor or knife and put into a 1.5 ml centrifugal tube. Excessive gel is removed to minimize the size of a gel slice.

2. 100 μl of buffer A2 (dissolution and adsorption buffer) is added to 100 mg of gel slice.

To 100 mg of gel, 100 μl of buffer A2 is added, but when agarose gel in a concentration of 2% or more is used, 600 μl of buffer B is added. The amount of gel which can be treated by one monolith column is 1000 mg, and therefore if the amount of gel exceeds 1000 mg, two or more monolith columns are used.

3. incubation is performed at 60° C. for 5 minutes or until the gel slice is fully dissolved. During incubation, the tube is subjected to vortexes twice to mix the solution. Agarose is fully dissolved. When gel in a concentration of 2% or more is used, the recovery rate increases if the incubation time is prolonged.

Subsequent operations are omitted, since they are same as the operations described in the above section "1. Micro-centrifugation method" of "A. Purification of PCR reaction solution using monolith solid phase column".

2. Vacuum Manifold Method

The monolith column can be operated by a vacuum manifold including a lure adapter. This protocol is designed for the purpose of purifying a DNA fragment from a standard or low-melt agarose gel (using TE or TBE buffer). Use of one monolith column and buffers for purification allows a fragment with 35 bp to 100 Kbp to be separated from a primer, a nucleotide, a polymerase, salts or the like by a sample treatment operation by a vacuum apparatus.

10 μl of buffer A2 (dissolution and adsorption buffer) is added to 10 mg of agarose gel. About 500 μl of buffer B (washing buffer) is used for washing.

Elution is carried out by a centrifugal operation by a desktop micro centrifugal machine at 10000 rpm or less.

A vacuum switch is temporarily turned off for each operation step so that uniform and stable vacuum is accomplished.

1. A target band is cut out by a clean razor or knife and put into a 1.5 ml centrifugal tube. Excessive gel is removed to minimize the size of a gel slice.

2. 100 μl of buffer A2 (dissolution and adsorption buffer) is added to 100 mg of gel slice.

To 100 mg of gel, 100 μl of buffer A2 is added, but when agarose gel in a concentration of 2% or more is used, 600 μl of buffer A1 is added. The amount of gel which can be treated by one monolith column is 600 mg, and therefore if the amount of gel exceeds 600 mg, two or more monolith columns are used.

3. Incubation is performed at 60° C. for 5 minutes or until the gel slice is fully dissolved. During incubation, the tube is subjected to vortexes twice to mix the solution. Agarose is fully dissolved. When gel in a concentration of 2% or more is used, the recovery rate increases if the incubation time is prolonged.

Subsequent operations are omitted, since they are same as the operations described in the above section "2. Vacuum manifold method" of "A. Purification of PCR reaction solution using monolith solid phase column".

C. The Following Method is Used for Purifying an Enzyme reaction solution using a monolith solid phase column.

1. Micro-Centrifugation Method

This protocol is designed for the purpose of purifying a double-strand DNA fragment from an enzyme reaction solution for restriction digestions, labeling reactions and the like. Use of a monolith column and buffers for purification allows a fragment with 35 bp to 100 Kbp to be separated from an enzyme, a primer, a nucleotide, salts or the like by a centrifugal operation.

30 μl of buffer A1 (adsorption buffer) is added to 10 μl of enzyme reaction solution. About 300 μl of buffer B (washing buffer) is used for washing.

All centrifugal operations are carried out by a general desktop micro centrifugal machine at 10000 rpm or less.

1. 3 parts by volume of buffer A1 are added to 1 part by volume of enzyme reaction solution and mixed. The maximum volume of the enzyme reaction solution which can be treated by a monolith column is 100 μl.

For example, 300 μl of buffer A1 is added to 100 μl of enzyme reaction solution.

Subsequent operations are omitted, since they are same as the operations described in the above section "1. Micro-centrifugation method" of "A. Purification of PCR reaction solution using monolith solid phase column".

2. Vacuum Manifold Method

The monolith column can be operated by a vacuum manifold including a lure adapter. This protocol is designed for the purpose of purifying a double-strand DNA fragment from an enzyme reaction solution for restriction digestions, labeling reactions and the like. Use of a monolith column and buffers for purification allows a fragment with 35 bp to 100 Kbp to be separated from an enzyme, a primer, a nucleotide, salts or the like by a sample treatment apparatus by a vacuum apparatus.

For example, 30 μl of buffer A1 (adsorption buffer) is added to 10 μl of enzyme reaction solution. About 300 μl of buffer B (washing buffer) is used for washing.

All centrifugal operations are carried out by a general desktop micro centrifugal machine at 10000 rpm or less.

A vacuum switch is temporarily turned off for each operation step so that uniform and stable vacuum is accomplished.

1. 3 parts by volume of buffer A1 are added to an enzyme reaction solution and mixed. The maximum volume of the enzyme reaction solution which can be treated by the monolith column is 100 μl.

For example, 300 μl of buffer A1 is added to 100 μl of enzyme reaction solution. Subsequent operations are omitted, since they are same as the operations described in the above section "2. Vacuum manifold method" of "A. Purification of PCR reaction solution using monolith solid phase column".

This advantage of the present invention in which adsorption and elution separation can be performed extremely easily, elution with a high-concentration salt is not necessary, and a nucleic acid can be purified extremely efficiently results from the adsorption of nucleic acid components on a monolith structure.

In methods of the conventional type, silica gel particles, glass particles and materials obtained by processing those particles into a filter form are used. In all of those methods, spaces through which the liquid passes pass along the surfaces of particles, and the liquid collides against particles to cause a turbulent flow, resulting in a nonuniform flow. Thus, all the liquid cannot uniformly contact the surfaces of particles. The monolith structure is an integral structure and has therein a continuous hole, and therefore it appears that the liquid passes through the inside of particles. That is, all the liquid uniformly contacts the structure. The skeletal structure is small as compared to particles, and no turbulent flow occurs after collision of the liquid, resulting in a uniform flow.

That is, in the conventional solid phase type, a turbulent flow occurs in particles, contact with the surface becomes nonuniform, and DNA on the low-molecular side is not adsorbed and falls out.

In the conventional type, the concentration of a chaotropic salt is increased to facilitate occurrence of a reaction for preventing the DNA from falling out. In this case, however, salt precipitation occurs and limitations arise, and therefore the collection of low-molecular DNA is limited.

In the monolith structure of the present invention, a uniform flow of liquid is ensured, and lower-molecular DNA can be adsorbed.

Of course, the same phenomenon occurs in the washing step. In the conventional method, a turbulent flow of a washing solution occurs to make it difficult to wash the surface of structure. As described in example 1, the undesired primers and the like remain after the first round of washing in the conventional method, while such components hardly remain in the method of the present invention.

The method using a filter having particles buried in fibers or the method using fibers themselves is the same in that a turbulent flow occurs.

As an example of the conventional method, an inorganic base material is placed near an outlet of a cylindrical hollow body having an inlet and an outlet, and the inorganic base material is held between tightly confined polyethylene frits (Japanese Patent Laid-open No. Heisei 8-501321)

In this case, it is the inorganic base material part that contributes to separation, and upper and lower frits are used for holding the inorganic material in the hollow body.

However tightly the frits are confined, spaces are generated between the frits and the inorganic material, and the liquid remains in the space portions. It is difficult to expel or replace the liquid in the space portions. Particularly, in the decompression method (the vacuum method) described above, if a gas phase portion is partly generated, the portion flows preferentially, and the liquid cannot be uniformly drawn. In the steps of absorption and washing of a sample, replacement of the liquid is hard to be performed.

In the final elution step, the liquid remains, resulting in Door collection.

In the monolith structure of the present invention, the macropore through which the liquid passes is a continuous body, and the liquid uniformly changes in the direction of flow. That is, the efficiency of replacement of the liquid is considerably improved. It can be considered that the aforementioned phenomenon is one of the factors that cause sample components to remain even after the second round of elution in the conventional type as shown in example 1. It can be understood that in the monolith structure of the continuous body of the present invention, the efficiency of replacement of the liquid is so high that one elution is enough and there are little residues after the second round of elution.

In the conventional type, the space changes depending on the degree of confinement, and variations among lots during confinement in the hollow body tend to occur. In the present invention, the monolith structure is an integral structure and no variations occur during confinement in the hollow body.

Frits and the inorganic material are further crushed into a united body although a product made by such a method is too expensive as a commercial product to actually exist, but in this method, different layers are formed in crushed interface portions. Likewise, the flow of a fluid is hindered as compared to the monolith structure having a uniform continuous hole.

Further, in the present invention, a hybrid having properties of silica and polyethylene can be prepared in a uniform phase if an inorganic material which is silica gel and an organic material such as polyethylene which is a frit material are mixed in a sol-gel step.

If the inorganic material is particulate, upper and lower frits are absolutely necessary to hold the particles, and the problem concerning the replacement efficiency as described above arises.

When a silica gel thin film in which silica fibers or gel particles are buried (e.g. M Pore Disk, manufactured by 3M) is used as an inorganic material, the thin film is poor in physical hardness, and may be deformed by centrifugal separation with rapid decompression or high speed rotation, resulting in elution of a part of fibers or particles. In slight deformation, the space volume changes, thus causing variations. In the monolith structure, due to separation by a continuous hole present in a hard body, deformation is not caused by pressure variations and the like, and therefore reproducibility can be secured.

Even if a hard fiber film or silica gel thin film which is not required to be held by frits can be formed, the liquid flows on the surface of fibers or gel, whereby a turbulent flow occurs, uniform separation cannot be achieved, and separation that would be achieved when using the monolith structure of the present invention cannot be expected.

Adsorption of low-molecular DNA and a high washing effect can be achieved only by the monolith structure free from a turbulent flow.

Further, flow paths in particles of the conventional type and micropores in the monolith structure of the present invention are different in the contact with the liquid flow. In the particle type or the like, the side of entrance of the liquid and the side of exit of the liquid are lacking in uniformity of the pressure in the liquid resistance, and are different in the contact of the liquid with the inside of the pore. In a pressurization system such as HPLC, the influence is low because the pressure can be made uniform, but a decompression system for use in the field of the present invention has a normal pressure on the inlet side and a negative pressure on the outlet side, and entrance to and exit from the inside of the pore in one particle becomes nonuniform. That is, some components enter the inside of the pore and the other components do not depending on component molecules although they are same components, and totally, the width at the time of elution increases. Therefore, it is difficult to eliminate only components to be removed at the time of washing, and in the finally eluted components, a primer on the low-molecular side remains as in the example of the conventional method shown in example 1. In the monolith structure of the present invention, the liquid always uniformly enters because there are micro-pores on the surface of the macro-pore through which the liquid flows. Therefore, the primer as a low-molecular impurity can be removed easily.

In the conventional method, it is conceivable that in large DNA, the liquid is hard to enter the pore, and further the viscosity of the liquid containing components increases, and therefore the contact becomes nonuniform, and two types of phenomena occur at the same time, and there are many portions that are not adsorbed. Furthermore, the possibility that high-molecular DNA is physically damaged and collapsed due to a turbulent flow increases.

Basically, by increasing the concentration of chaotropic salts, these phenomena can be alleviated, but the salt is not removed at the time of washing, and is eluted at the time of elution. That is, a large amount of salts exits in sample components after purification. This leads to a serious problem in subsequent use.

The method of the present invention using a monolith structure is very effective, since the salt concentration can be decreased and the aforementioned problems can be solved. Further, the method becomes more effective if a potassium salt having a stronger cation exchange action is used in combination. The potassium salt has a strong cation exchange action and therefore contributes to adsorption of a nucleic acid on the surface, but for this reason, target purified DNA is not eluted if the potassium salt remains on the surface at the time of elution, and therefore reliable washing is absolutely necessary. In the particle type, a turbulent flow occurs at the time of washing, and further, entrance into the pore is non-uniform, and therefore a portion where the potassium salt remains in a high concentration on the base inevitably appears. As a measure, a buffer capable of removing potassium, specifically another salt may be added to an elution liquid, but this is not suitable for the purpose of a subsequent application.

In the monolith structure, the potassium salt acts effectively, since the uniform flow of a liquid and the uniform entrance into a pore are possible.

EXAMPLES

Example 1

In purification of a PCR reaction solution (fragment DNA), 50 μl of PCR amplification reactant is mixed with 300 μl of buffer A1 (1 M guanidine hydrochloride, 0.2 M potassium acetate, 50% 2-propanol). A silica monolith solid phase column 9 is inserted into a collection tube 8, and the mixture is injected into the silica monolith solid phase column 9, and centrifuged in a 1.5 ml centrifuging tube. The silica monolith solid phase column 9 is subjected to a washing treatment with a B buffer (0.2 M potassium acetate, 50% ethanol) so as not to contain a salt.

For elution, 20 μl of buffer C for elution (EDTA 4 mM, Tris-HCl 10 mM, pH 8; or sterile DNA/RNA free water) is passed through the silica monolith solid phase column for centrifugation with another 1.5 ml centrifuging tube to perform centrifugal separation. A PCR product thus purified (fragment DNA) contains no primer, dNTPs, polymerase and salts, and can be used directly in a subsequent operation. (See FIGS. 1 and 2) In FIG. 1, M: molecular weight marker; (1) sample purified by the conventional method; and (2): sample purified in the present invention.

Figure 1:
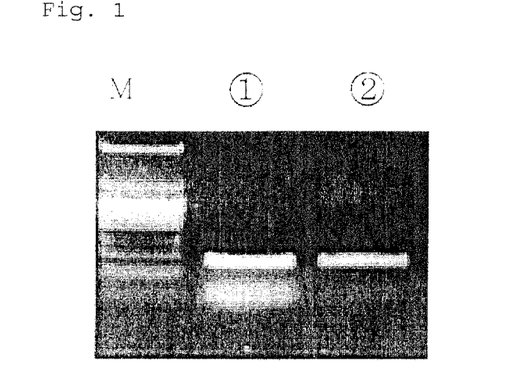
FIG. 1 is a view of contrast of example 1 according to the present invention with a conventional method.
Figure 2:
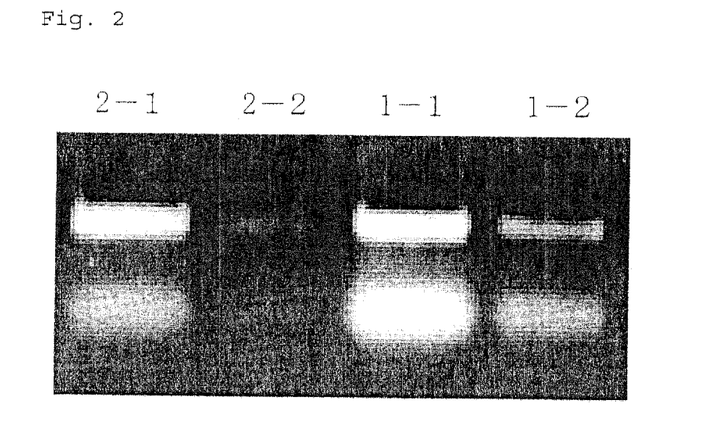
FIG. 2 is a view of contrast of example 1 according to the present invention with the conventional method.
Figure 3:
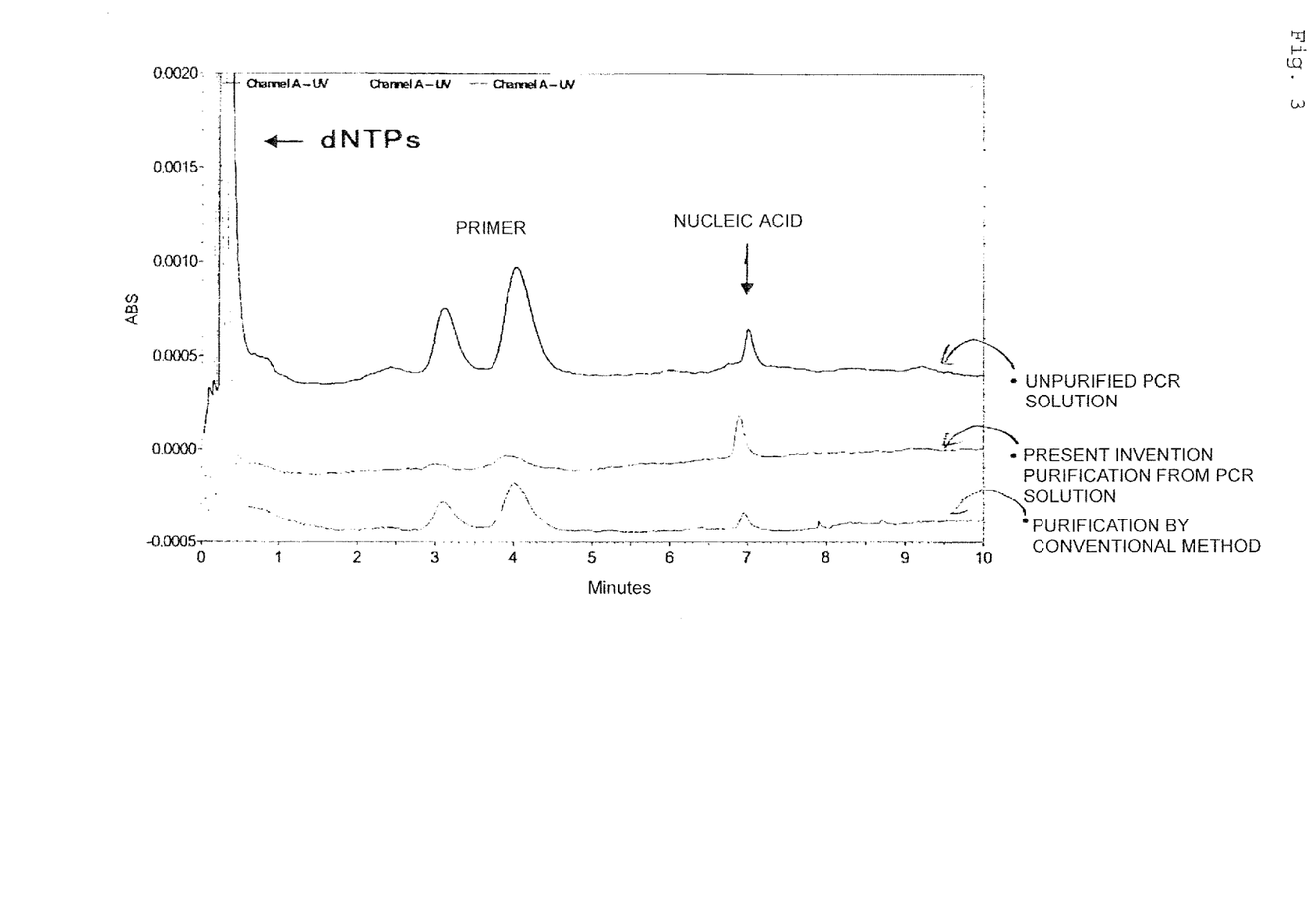
FIG. 3 is a view of evaluation by HPLC in example 1 of the present invention.
Figure 4:
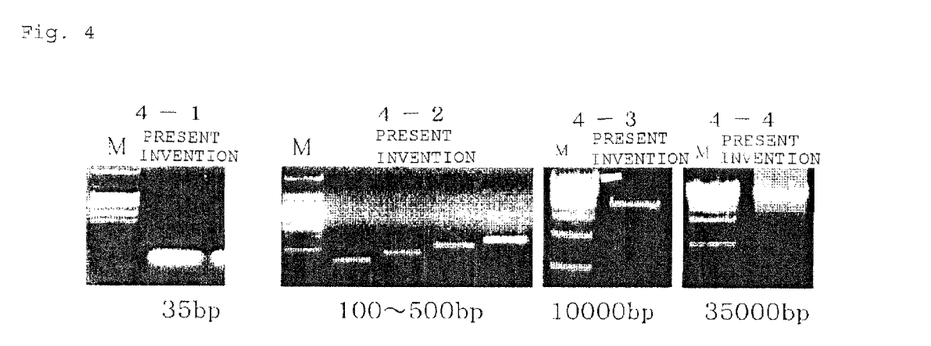
FIG. 4 is a view of purification and separation of DNA fragments in example 2 according to the present invention.

Symbol (1) corresponds to the evaluation by electrophoresis with a sample purified by the conventional method in Japanese Patent Laid-open No. Heisei 8-501321 (400 bp). Symbol (2) corresponds to the method of the present invention. In the result of (1), a portion on the low-molecular side (lower) remains in a large quantity, while in the result of (2), such a portion hardly remains, and high purification efficiency is obtained. In FIG. 2, symbols 1-1 and 1-2 correspond to the results of performing elution twice by the conventional method and observing the residues, and symbols 2-1 and 2-2 correspond to the results by the present invention. It is apparent that in the present invention, residues hardly remain after the first elution, and high purification efficiency can be obtained. FIG. 3 shows the evaluation using HPLC. The conditions of HPLC are shown below.

Conditions of HPLC
Column: CIM DEAE
Eluent:
A: 20 mM Tris-HCl pH 7.4
B: A+1M NaCl
A/B=50/50–(10 MIN)–0/100
Flow rate: 3 ml/min
Detection: UV 260 nm In FIG. 3, HPLC evaluation data of an unpurified PCR solution is the uppermost chromatogram, and it is apparent that there is a less change in pattern as compared to the chromatogram (lowermost) of purification by the conventional method in Japanese Patent Laid-open No. Heisei 8-501321, and dNTPs and primers are hardly removed. In the method of the present invention, it is apparent that two peaks of the dNTPs and primers are considerably removed as in the second chromatogram and a target nucleic acid is highly purified (see FIG. 3).

Example 2

In purification of fragment DNA from agarose gel, a PCR amplification product is electrophoresed using standard or low-melt agarose gel (using a TE or TBE buffer), and DNA is separated in agarose gel (0.5% of TE or TBE). DNA fractions to be isolated are cut out from the gel by a clean razor or knife, and put into a 1.5 ml centrifuging tube. They are mixed with 300 μl of buffer A2 (2M guanidine thiocyanic acid, 0.4 M potassium acetate, 30% 2-propanol), and incubated at 60° C. for 5 minutes or until gel slices are fully dissolved.

For this solution, the solution is injected into the monolith solid phase column 9 attached to the collection tube 8 and centrifuged in a 1.5 ml centrifuging tube in accordance with example 1. The monolith solid phase column 9 is washed by buffer B (0.2 M potassium acetate, 50% ethanol) so as not to contain a salt.

For elution, 20 μl of buffer C (EDTA 1 mM, Tris-HCl 10 mM (pH 8); or sterile DNA/RNA free water) is passed through a column for centrifugation with another 1.5 ml centrifuging tube to perform centrifugal separation. Among FIGS. 4-1 to 4-4, FIG. 4-1 shows the evaluation by electrophoresis of 35 bp, FIG. 4-2 shows the evaluation by electrophoresis of 100 to 500 bp, FIG. 4-3 shows the evaluation by electrophoresis of 10000 bp, and FIG. 4-4 shows the evaluation by electrophoresis of 35000 bp.

In the method of the present invention, low-molecular parts of 35 bp to about 100 Kbp were collected, and it is apparent that a wide range of DNAs can be purified from agarose gel. Similar results were obtained even with water containing no EDTA buffer as an elution buffer,

Example 3

100 μg of DNA is treated with a restriction enzyme. The DNA restriction digested solution was mixed with 300 μl of buffer A1 in accordance with example 1, and the subsequent treatments were carried out in the same manner as in example 1. The purified DNA obtained after elution contained no restriction enzyme and salts, and the absorbance determination ratio 260/280 was 1.8, which is a satisfactory value.

Example 4

In purification of a PCR product of 35 bp having a small molecular size, 10 μl of PCR reactant was mixed with 100 μl of buffer A1 in accordance with example 1, and subsequent treatments were carried out in the same manner as in example 1. (See FIG. 5) In the figure, M: molecular weight marker; 1: sample before purification; and 2: sample purified in the present invention.

Figure 5:
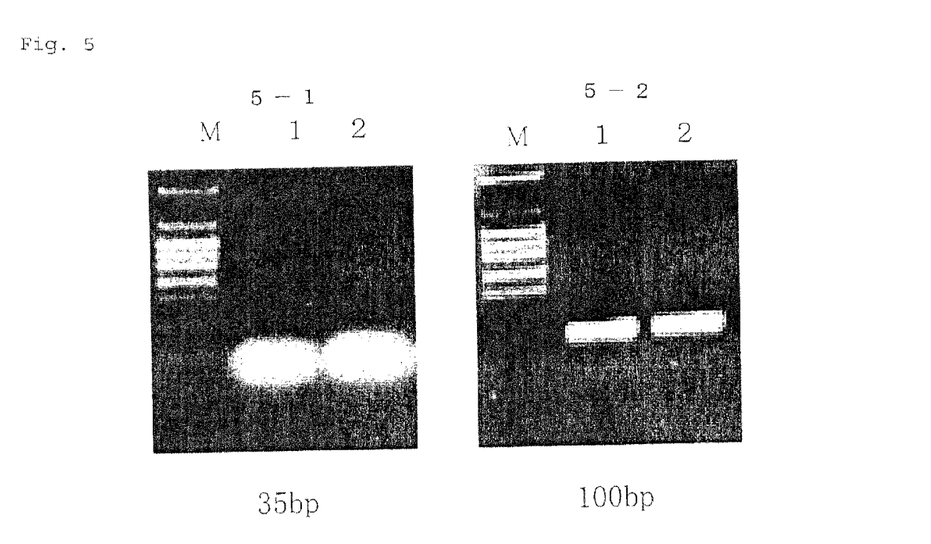
FIG. 5 is a view of purification and separation of DNA fragments in example 4 according to the present invention.

Here, small DNA of 100 bp or less, purification could be purified from a PCR reaction solution of DNA of 35 bp.

Example 5

In purification of a PCR product having a large molecular size (100 bp to 100000 bp), 20 μl of PCR reactant was mixed with 200 μl of buffer A1 in accordance with example 1, and subsequent treatments were carried out in the same manner as in example 1. (See FIG. 6) In the figure, M: molecular weight marker; 1: sample before purification; 2: sample purified in the present invention.

Figure 6:
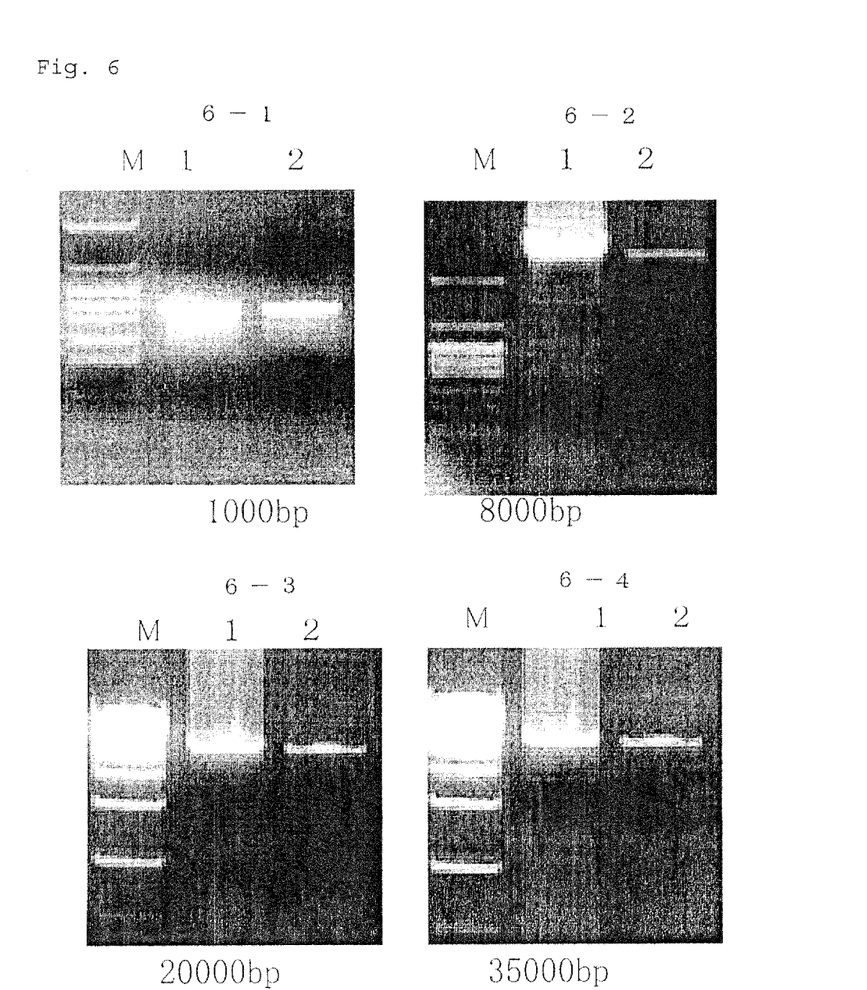
FIG. 6 is a view of purification and separation of DNA fragments in example 5 according to the present invention.

DNA of 1000 bp to 100 Kbp could be purified from a PCR reactant.

Example 6

In purification of a single-strand DNA, 20 µl of solution was mixed with 200 µl of buffer A1 in accordance with example 1, and subsequent treatments were carried out in the same manner as in example 1. (See FIG. 7) In the figure, M: molecular weight marker; 1: sample before purification; and 2: sample purified in the present invention; and 3: sample purified by the conventional method.

Figure 7:
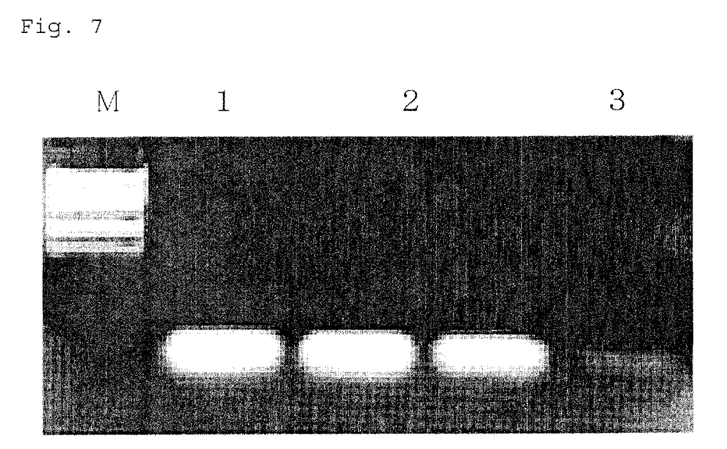
FIG. 7 is a view of separation of a single-strand PCR amplification product in example 6 according to the present invention.

Single-strand DNA of 35 mer could not be collected in the conventional method (3), but could be collected in good reproducibility at two times in the present invention (2).

Example 7

Comparison between purification with sodium and purification with potassium (retention mechanism) (See FIG. 8) In the figure, N: molecular weight marker; 1: sample after purification with glass monolith and potassium; 2: sample after purification with silica monolith and potassium; and 3: sample after purification with silica monolith and sodium.

Figure 8:
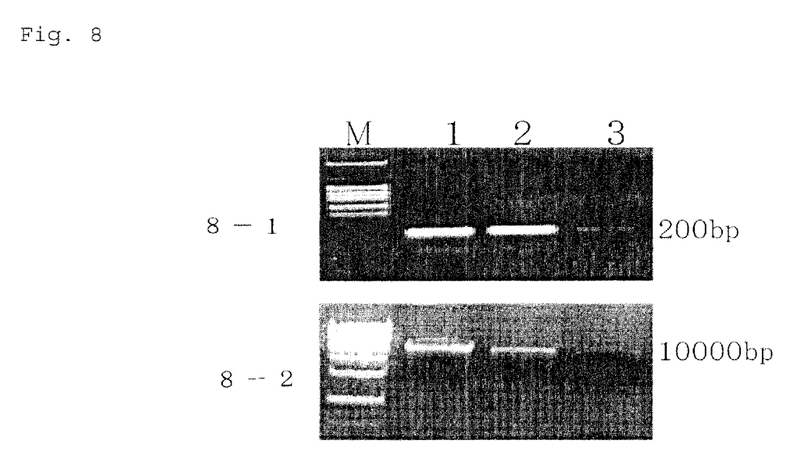
FIG. 8 is a view of comparison of purifications with sodium and potassium in example 7 according to the present invention.

Purification with sodium which had been often used was compared with purification with potassium having an effect of the present invention. Retention could hardly be achieved with sodium, and high purification efficiency could be obtained with potassium. For the glass monolith, higher purification efficiency could be obtained with potassium as in the silica monolith.

Carrying out the following method for making the present invention effective is meaningful.

A method for separating and purifying DNA, characterized in that corresponding nucleic acids are adsorbed in through-pores (macro-pore) of an integral monolith structure, respectively, by interposing alkali metal salts in a solution containing nucleic acid, the monolith structure is washed with a washing solution, and the nucleic acids are then eluted.

The method for separating and purifying DNA, characterized in that the alkali metal salt is potassium acetate.

The method for separating and purifying DNA, characterized in that a dissolution and adsorption buffer containing 0.1 M to 1 M of potassium acetate is used.

The method for separating and purifying DNA, characterized in that dissolution and adsorption is carried out with a dissolution and adsorption buffer containing a guanidine salt or a potassium salt such as potassium acetate.

The method for separating and purifying DNA, characterized in that elution is carried out with water containing Tris-HCl and EDTA.

The method for separating and purifying DNA, characterized in that dissolution, adsorption, separation and washing operations are carried out using one monolith solid phase column.

Kit consisting of a dissolution and adsorption buffer, water and a separation and purification mechanism.

INDUSTRIAL APPLICABILITY

As described above, the mechanism of separating and purifying DNA and the like according to the present invention is frequently used in studies of molecular biology, and is especially useful for purification of fragment DNA or the like performed prior to applications of PCR, cloning, sequencing, restriction enzyme digestion, other enzyme actions and the like, and can quantitatively separate and efficiently purify a wide range of DNAs of 35 bp (mer) to 100 Kbp (mer), and adapt to purification of a wide range of nucleic acids.

What is claimed is:

1. An apparatus for separating and purifying nucleic acids comprising an integral monolith structure, wherein the monolith structure is a glass or a silica, and further comprising macro-pores continuously extending from one end of the monolith structure to the other end, wherein the said monolith structure contains micro-pores in the macro-pores, and the diameter of the micro-pores is less than or equal to 100 nm and allowing a solution containing nucleic acids to be separated to pass therethrough, wherein the diameter range of the macro-pores is selected according to the size of the nucleic acid to be purified and wherein the size range is selected from the group consisting of diameters of about 10 nanometers (nm) to about 100 nm configured to separate nucleic acids of 35 base pairs (bp) to 300 bp in length, diameters of about 100 nm to about 1 micrometers (µm) configured to separate nucleic acids of 300 bp to 3 kilobase pairs (Kbp) in length, diameters of about 1 µm to about 10 µm configured to separate nucleic acids of 3 Kbp to 30 Kbp in length, and diameters of about 10 µm to about 100 µm configured to separate nucleic acids of 30 Kbp to 300 Kbp in length.

2. The apparatus for separating and purifying nucleic acids according to claim 1, wherein a disc formed with the monolith structure is placed in a column tube to form a monolith solid phase column.

3. The apparatus for separating and purifying nucleic acids according to claim 2, wherein the apparatus employs a monolith solid phase column formed by detachably attaching a base formed with the monolith structure to a cylindrical body having the top and the bottom opened.

4. The apparatus for separating and purifying nucleic acids according to claim 1, wherein the apparatus employs a monolith solid phase column formed by detachably attaching a base formed with the monolith structure to a cylindrical body having the top and the bottom opened.

* * * * *